United States Patent
Aichert et al.

(10) Patent No.: US 10,977,839 B2
(45) Date of Patent: Apr. 13, 2021

(54) METHOD AND DEVICE FOR DETERMINING A GEOMETRY CALIBRATION FOR AN IMAGING DEVICE AND ALSO METHOD FOR DETERMINING ASSIGNMENT DATA FOR THE GEOMETRY CALIBRATION

(71) Applicant: Siemens Healthcare GmbH, Erlangen (DE)

(72) Inventors: Andre Aichert, Erlangen (DE); Andreas Maier, Erlangen (DE); Tobias Wuerfl, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 74 days.

(21) Appl. No.: 16/407,436

(22) Filed: May 9, 2019

(65) Prior Publication Data
US 2019/0355156 A1    Nov. 21, 2019

(30) Foreign Application Priority Data
May 16, 2018   (EP) .................................... 18172655

(51) Int. Cl.
  *G06T 11/00*   (2006.01)
  *G06T 7/00*    (2017.01)
  *G06T 15/08*   (2011.01)

(52) U.S. Cl.
  CPC .......... *G06T 11/005* (2013.01); *G06T 7/0014* (2013.01); *G06T 15/08* (2013.01);
  (Continued)

(58) Field of Classification Search
  CPC ..... G06T 11/005; G06T 7/0014; G06T 15/08; G06T 2207/10116; G06T 2207/30004; A61B 6/584; A61B 6/583; A61B 6/585
  See application file for complete search history.

(56) References Cited

U.S. PATENT DOCUMENTS

| | | | |
|---|---|---|---|
| 10,820,876 B2 * | 11/2020 | Ritter | A61B 6/032 |
| 2003/0058999 A1 * | 3/2003 | Mitschke | G01N 23/046 378/207 |

(Continued)

FOREIGN PATENT DOCUMENTS

WO    WO 0187136 A2    11/2001

OTHER PUBLICATIONS

Hartley, Richard et al. "Multiple View Geometry in Computer Vision" Cambridge University Press, ISBN: 0521623049, Jun. 2000.

(Continued)

*Primary Examiner* — Aaron W Carter
(74) *Attorney, Agent, or Firm* — Harness, Dickey & Pierce, P.L.C.

(57) ABSTRACT

A method for determining assignment data is carried out in a method for determining a geometry calibration. The 3D calibration phantom features a calibration object with a number of calibration elements, which are arranged so that a descriptor based on the spatial arrangement is projectively invariant. Based upon the descriptor the calibration elements mapped in the 2D transmission element can be assigned to the calibration elements of the calibration object, so that the geometry calibration is determined on the basis of this assignment and the arrangement of the calibration elements in the three-dimensional space as well as on the 2D image.

16 Claims, 6 Drawing Sheets

(52) U.S. Cl.
CPC ............... *G06T 2207/10116* (2013.01); *G06T 2207/30004* (2013.01)

(56) References Cited

U.S. PATENT DOCUMENTS

| | | |
|---|---|---|
| 2003/0088179 A1 | 5/2003 | Seeley et al. |
| 2017/0074808 A1 | 3/2017 | Bernard et al. |
| 2017/0103505 A1 | 4/2017 | Demri et al. |
| 2017/0172533 A1* | 6/2017 | Raupach ................ A61B 6/032 |
| 2017/0352166 A1* | 12/2017 | Raupach ............... G06T 11/005 |
| 2019/0355156 A1* | 11/2019 | Aichert ................. G06T 7/0014 |
| 2020/0261050 A1* | 8/2020 | Bornefalk .............. A61B 6/482 |

OTHER PUBLICATIONS

Meer, Peter et al. "Efficient Invariant Representations" International Journal of Computer Vision, vol. 26, No. (2), pp. 137-152, 1998.

Strobel, Norbert et al. "Improving 3D Image Quality of X-ray C-Arm Imaging Systems by Using Properly Designed Pose Determination Systems for Calibrating the Projection Geometry" Medical Imaging 2003: Physics of Medical Imaging, Proceedings of SPIE, vol. 5030, pp. 943-954, 2003.

Loy, Gareth et al. "Fast Radial Symmetry for Detecting Points of Interest" IEEE Transactions on Pattern Analysis and Machine Intelligence, vol. 25, No. 8, pp. 959-973, Aug. 2003.

European Search Report for Germany. European Patent Application No. EP18172655, dated Nov. 5, 2018.

\* cited by examiner

METHOD AND DEVICE FOR DETERMINING A GEOMETRY CALIBRATION FOR AN IMAGING DEVICE AND ALSO METHOD FOR DETERMINING ASSIGNMENT DATA FOR THE GEOMETRY CALIBRATION

PRIORITY STATEMENT

The present application hereby claims priority under 35 U.S.C. § 119 to European patent application number EP18172655.5 filed May 16, 2018, the entire contents of each of which are hereby incorporated herein by reference.

FIELD

Embodiments of the invention generally lie in the field of transmission imaging and relate in particular to a method for determining a geometry calibration for an imaging device, a device for determining a geometry calibration for an imaging device, a 3D calibration phantom for determining a geometry calibration and for determining assignment data for a geometry calibration as well as to a method for determining assignment data for geometry calibration of an imaging device.

BACKGROUND

In transmission imaging, to create a transmission image, radiation is conveyed through an object to be examined and, after passing through the object to be examined, strikes a 2D detector. Such transmission imaging is known in particular from computed tomography. In such cases the imaging device is a computed tomography unit, which, as a radiation source, usually has an x-ray source and which usually detects via its 2D detector the extent to which the (x-ray) radiation has been changed, in particular has been absorbed, by the object to be examined.

In computed tomography systems there is a trend towards more open and thus in particular more flexible systems. Thus current C-arms, somewhat differently from conventional computed tomography systems, move with a robot arm, to which the radiation source and the 2D detector is attached, around the object to be examined. In this way rigid tubes are not required and therefore such systems usually need less space and can be used more flexibly—which is especially relevant in applications such as interventional use or in materials testing of a diversity of parts in industry. However the geometry of such systems is usually—for instance as a result of mechanical restrictions—not a perfect arc of a circle or a perfect spiral and/or is less precisely known.

In imaging systems of which the exact geometry and/or imaging characteristics—for instance because of mechanical restrictions and/or their method of operation—are not known exactly, but which image the objects to be examined in a reproducible way, a geometric calibration is able to be carried out. In this way, the radiation source and the 2D detector of a computed tomography system with C-arm can be moved in a reproducible way around the object to be examined and in this way reproducible images, i.e. in particular with reproducible errors, can be created.

A geometric calibration allows these reproducible errors to be compensated for. The data for a geometry calibration required for such a geometric calibration—abbreviated to geometry calibration—is usually determined by a dedicated recording of a known and exactly made test object (a so-called 3D calibration phantom) for each individual image—thus for each view of the 3D calibration phantom and its respective 2D transmission image. Typically such a 3D calibration phantom has a number of exactly positioned metal spheres, such as for example the PDS2 from N. K. Strobel et al, Improving 3D Image Quality of X-Ray C-Arm Imaging Systems by Using Properly Designed Pose Determination Systems for Calibrating the Projection Geometry, Proceedings of SPIE.

It should be noted that in a 2D transmission image the metal spheres usually used for a 3D calibration phantom all appear the same, i.e. in particular in computed tomography only their respective shadows are visible in the x-ray radiation, so that the spheres cannot be distinguished from one another. In the algorithms for geometric calibration usually used one is restricted to a few 3D calibration phantoms and also to trajectories specifically adapted for the phantoms—i.e. in particular tracks for particular views and thus 2D transmission images of the respective 3D calibration phantom from different positions of the 2D detector and/or of the radiation source. A restriction also arises on those spatial extents for which such calibration phantoms are present.

SUMMARY

The inventors have discovered that a need exists for improving the geometric calibration and, in doing so, in particular to make it easier to produce a 3D calibration phantom and/or to design it more flexibly and/or to reduce the restrictions during the geometric calibration and when such calibration is being carried out.

Embodiments of the invention are directed to a method for determining assignment data for an imaging device, a 3D calibration phantom for determining a geometry calibration and assignment data for an imaging device, a method for determining a geometry calibration for an imaging device and by a device for determining a geometry calibration for an imaging device through the teaching of one of the main claims in each case. Advantageous forms of embodiment, developments and variants of the present invention are in particular the subject matter of the claims.

A first embodiment of the invention relates to a method for determining assignment data for an imaging device, in which, in a transmission imaging, after passing through a 3D calibration phantom for creating a 2D transmission image of the 3D calibration phantom, radiation strikes a 2D detector. The 3D calibration phantom has at least one calibration object with a predetermined number of physical calibration elements, which are spatially arranged such that a descriptor based on the spatial arrangement is projectively invariant during the transmission imaging. In this case, in a few variants, the descriptor can moreover be based on that fact that one or more of the physical calibration elements is embodied so that—even in the 2D transmission image—these differ from the usual physical calibration elements.

A second embodiment of the invention relates to a 3D calibration phantom for determining a geometry calibration and assignment data for an imaging device. In the imaging device, in a transmission imaging, after passing through the 3D calibration phantom, radiation strikes a 2D detector to create a 2D transmission image of the 3D calibration phantom. The 3D calibration phantom has at least one calibration object with a predetermined number of physical calibration elements, which are arranged spatially in such a way that a descriptor based on the spatial arrangement is projectively invariant under the transmission imaging. Overall the 3D calibration phantom has at least seven physical calibration elements. In this case the physical calibration elements feature a material that is opaque for the radiation and/or that absorbs or scatters the radiation.

A third embodiment of the invention relates to a method for determining a geometry calibration for an imaging device. In the imaging device, in a transmission imaging, after passing through a 3D calibration phantom, radiation strikes a 2D detector for creating a 2D transmission image of the 3D calibration phantom. In this case the 3D calibration phantom is embodied according to the second embodiment of the invention.

A fourth embodiment of the invention relates to a device for determining a geometry calibration for an imaging device. In the imaging device, in a transmission imaging, after passing through a 3D calibration phantom, radiation strikes a 2D detector to create a 2D transmission image of the 3D calibration phantom. In this case the 3D calibration phantom is embodied in accordance with the second embodiment of the invention. The device has a data processing device and a data interface. In this case the data interface is configured to receive 2D transmission images from the imaging device. Finally the device is configured to carry out a method in accordance with the third embodiment of the invention.

A further embodiment of the invention relates to a calibratable, imaging system, which features a device in accordance with the fourth embodiment of the invention and features an imaging device. In this case, in a few variants, the imaging device can be embodied as a computed tomography system or as the imaging part of a computed tomography system and/or the system can be embodied as the computed tomography system, which is configured to carry out a method in accordance with the third embodiment of the invention.

A further embodiment of the invention relates to a method for determining assignment data for an imaging device, in which, in a transmission imaging, after passing through a 3D calibration phantom, radiation strikes a 2D detector to create a 2D transmission image of the 3D calibration phantom, the 3D calibration phantom including at least one calibration object with a number of physical calibration elements, spatially arranged such that a descriptor based on the spatial arrangement is projectively invariant during the transmission imaging, the method comprising:

provisioning the 2D transmission image, the at least one calibration object, of the 3D calibration phantom, being shown in the 2D transmission image provisioned;

recognizing the number of physical calibration elements shown in the 2D transmission image to determine calibration elements recognized in the 2D transmission image and a 2D arrangement of the calibration elements;

determining subsets of the physical calibration elements recognized, a number of subsets determined corresponding to the number of physical calibration elements of the at least one calibration object;

calculating a respective descriptor, relating to respective calibration elements for each subset of the subsets determined; and determining the assignment data, the recognized calibration elements of each subset being assigned to the physical calibration elements of the at least one calibration object, for which the respective descriptor computed, and a descriptor relating to the physical calibration elements, differ from one another.

A further embodiment of the invention relates to a 3D calibration phantom for determining a geometry calibration and assignment data for an imaging device, for which, in a transmission imaging, after passing through the 3D calibration phantom, radiation strikes a 2D detector to create a 2D transmission image of the 3D calibration phantom, the 3D calibration phantom comprising:

at least one calibration object including a number of physical calibration elements, spatially arranged such that a descriptor based on a spatial arrangement is projectively invariant during the transmission imaging; and the number of physical calibration elements including at least seven physical calibration elements, featuring a material, the material being at least one of opaque for the radiation and scattering or absorbing the radiation.

A further embodiment of the invention relates to a method for determining a geometry calibration for an imaging device in which, in a transmission imaging, after passing through a 3D calibration phantom, radiation strikes a 2D detector to create a 2D transmission image of the 3D calibration phantom, the method comprising:

provisioning the 2D transmission image, in which at least one calibration object of the 3D calibration phantom is shown;

assigning calibration elements recognized in the 2D transmission image to physical calibration elements of the 3D calibration phantom;

provisioning 3D arrangement data for the geometry calibration, characterizing a 3D arrangement of the physical calibration elements; and determining projection data of the geometry calibration for the 2D transmission image based upon the 3D arrangement data, of the calibration elements assigned to the physical calibration elements and recognized in the 2D transmission image, and the 2D arrangement of the recognized calibration elements.

A further embodiment of the invention relates to a device for determining a geometry calibration for an imaging device in which, in a transmission imaging, after passing through a 3D calibration phantom, radiation strikes a 2D detector to create a 2D transmission image of the 3D calibration phantom, the device comprising:

a data processing device;

a data storage device; and a data interface, configured to receive 2D transmission images from the imaging device the data storage device storing computer readable instructions and the data processing device being configured to execute the computer readable instructions such that the data processing device is configured to perform at least:

provisioning the 2D transmission image, in which at least one calibration object of the 3D calibration phantom is shown;

assigning calibration elements recognized in the 2D transmission image to physical calibration elements of the 3D calibration phantom;

provisioning 3D arrangement data for the geometry calibration, characterizing a 3D arrangement of the physical calibration elements; and determining projection data of the geometry calibration for the 2D transmission image based upon the 3D arrangement data, of the calibration elements assigned to the physical calibration elements and recognized in the 2D transmission image, and the 2D arrangement of the recognized calibration elements.

A further embodiment of the invention relates to a non-transitory computer readable storage medium storing a computer program including program segments which, when executed by a computer, cause the computer to perform an embodiment of the method.

Further advantages, features and possible applications emerge from the more detailed description given below of example embodiments and/or from the figures.

BRIEF DESCRIPTION OF THE DRAWINGS

The invention is explained in greater detail below with reference to the figures on the basis of advantageous example embodiments. The same elements or components of the example embodiments are essentially labeled by the same reference characters, if the description does not state otherwise or unless the context dictates otherwise.

In the figures, in some cases in schematic diagrams.

Figure 1:
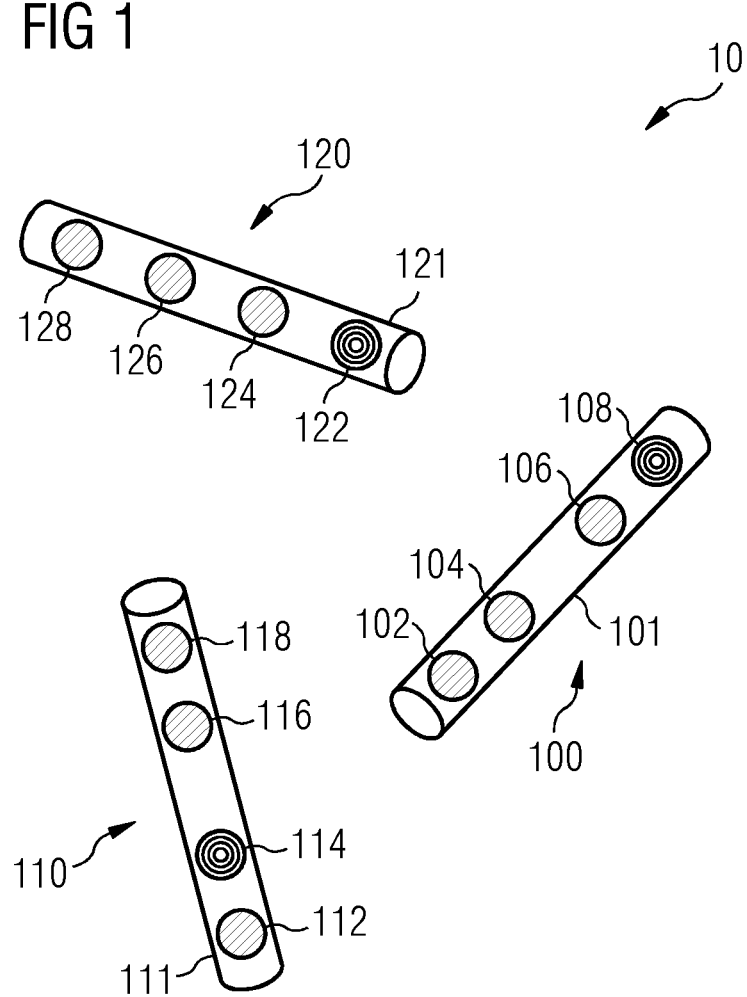
FIG. 1: shows a 3D calibration phantom according to a form of embodiment.

The figures are schematic diagrams of different forms of embodiment and/or example embodiments of the present invention. Elements and/or components shown in the figures are not necessarily shown true-to-scale. Instead the various elements and/or components shown in the figures are reproduced such that their function and/or their purpose are able to be understood by the person skilled in the art.

Connections and couplings between functional units and elements shown in the figures can also be implemented as indirect connections or couplings. In particular data connections can be embodied wired or wireless. Also it can be that specific connections, such as electrical connections, such as for energy supply, are not shown for the sake of simplicity.

DETAILED DESCRIPTION OF EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the invention relates to a method for determining assignment data for an imaging device, in which, in a transmission imaging, after passing through a 3D calibration phantom for creating a 2D transmission image of the 3D calibration phantom, radiation strikes a 2D detector. The 3D calibration phantom has at least one calibration object with a predetermined number of physical calibration elements, which are spatially arranged such that a descriptor based on the spatial arrangement is projectively invariant during the transmission imaging. In this case, in a few variants, the descriptor can moreover be based on that fact that one or more of the physical calibration elements is embodied so that—even in the 2D transmission image— these differ from the usual physical calibration elements.

The method of at least one embodiment has the following features. In the method the 2D transmission image is provided in which the at least one calibration object of the 3D calibration phantom is shown. Moreover in the method the physical calibration elements shown in the 2D transmission image are recognized for determining calibration elements recognized in the 2D transmission image and their 2D arrangement.

In the method subsets of the recognized calibration elements are determined, of which the number of calibration elements corresponds in each case to the predetermined number of physical calibration elements of the at least one calibration object. For each subset the descriptor relating to the calibration elements in is computed each case. Finally the assignment data is determined, by the recognized calibration elements of each subset being assigned to the physical calibration elements of the at least one calibration object, for which the computed descriptor and the descriptor relating to the physical calibration elements differ by the least from one another.

A "calibration element" in the sense of embodiments of the invention is to be understood as at least a part of a calibration object and/or of a 3D calibration phantom, wherein the part is embodied and in particular features such a material that the radiation is influenced by the calibration element and an image of the calibration element occurs in the 2D transmission image. With x-ray radiation as the radiation—such as in computed tomography—the calibration element can be made from a metal. The calibration element can also be shaped like a sphere with a specific spatial extent.

A "descriptor" in the sense of embodiments of the invention is, inter alia, to be understood as at least one item of information for a calibration object, which characterizes this calibration object. In such cases this information can comprise properties of the spatial arrangement of the calibration elements of this calibration object. Depending on the degree of characterizing force of the information—i.e. of the descriptor—for this calibration object, the descriptor is also referred to as a weak or a strong descriptor. In this case a weak descriptor can have the same information for different calibration objects, whereby it is not possible to uniquely identify the calibration object. Conversely a strong descriptor can be embodied, i.e. the information can be selected, so that—in particular with a restricted number or type of calibration objects—the calibration objects are each able to be identified (uniquely) via this strong descriptor.

One advantage of determining the assignment data can lie in particular in the fact that the calibration elements recognized in the 2D transmission image can be assigned to the physical calibration elements of the at least one calibration object of the 3D calibration phantom, whereby, for the geometric calibration—i.e. in particular for determining a geometry calibration—algorithms from computer vision can be employed. These types of algorithms from computer vision are based on the fact that the objects mapped in an image can be assigned to their physical objects. However since usually the calibration elements used in the transmission imaging all have at least essentially the same images, i.e. in particular are at least essentially the same in the 2D transmission image, the algorithms from computer vision cannot be applied directly.

Instead it is only the determination of the assignment data that makes it possible to transfer these algorithms to the geometric calibration during the transmission imaging. On the basis of the descriptor, which is projectively invariant during the transmission imaging, the calibration objects or the at least one calibration object of the 3D calibration phantom are able to be identified—at least statistically—independently of the respective view, i.e. in particular from the projection of the at least one calibration object onto the 2D transmission image. Thus an assignment of the at least one calibration object and its image is advantageously made possible in the 2D transmission image, whereby in particular the calibration elements of the at least one calibration object can also be assigned to their respective images.

This means that there is in particular no longer any restriction to a few exactly-produced calibration phantoms and corresponding trajectories, which make possible an assignment of the elements of the calibration phantom to the respective images thereof under the views of the respective trajectories. Without this restriction a 3D calibration phantom can be adapted in particular to the objects to be examined—such as by arranging a number of calibration objects distributed in space and/or close to the expected edges of the objects to be examined—whereby a more exact calibration for these objects to be examined is made possible.

In a few forms of embodiment the 3D calibration phantom features a plurality of calibration objects, wherein the at least one calibration object and a further calibration object are each part of the plurality of calibration objects. Moreover the calibration objects of the plurality of calibration objects each have a predetermined number of physical calibration elements, which are arranged spatially in such a way that a descriptor based on the spatial arrangement is projectively invariant during the transmission imaging, wherein the descriptor is a strong descriptor. An advantage of such a strong descriptor can in particular lie in the fact that the calibration objects of the plurality of calibration objects are able to be identified (in particular uniquely) on the basis of the strong descriptor, which is thus a strong descriptor for this plurality.

In a few forms of embodiment, for which the 3D calibration phantom has a plurality of calibration objects, the method is embodied correspondingly for the physical calibration elements of the calibration objects of the plurality of calibration objects. Moreover the method features an identification of the individual calibration objects of the plurality of calibration objects based on the strong descriptor.

In a few forms of embodiment of the method, for which the at least one calibration object has four physical calibration elements, which are arranged at least essentially along a first straight line, the descriptor can feature an arrangement of the recognized calibration elements at least essentially along a 2D straight line and also a double ratio for the spacings between the recognized calibration elements. In the method, in the determination of the subsets, those subsets are determined for which the four recognized calibration elements of the respective subset are arranged at least essentially along a 2D straight line in the 2D transmission image.

Moreover the descriptor is computed for each subset by way of the double ratio for the spacings between the four recognized calibration elements. An advantage of this descriptor can in particular lie in the fact that it has two items of information—namely that the calibration elements are arranged along a 2D straight line in the transmission image or along a 3D straight line for the 3D calibration phantom, and features the double ratio, which are each projectively invariant and which initially, on the basis of the arrangement along the straight line make possible an efficient division into subsets and subsequently—provided the calibration objects of the 3D calibration phantoms are chosen so that the double ratios of the calibration objects differ—make possible a distinction and thereby identification of the calibration objects and their calibration elements and thus in particular an assignment of the physical calibration elements to their images in the 2D transmission image. The double ratios can also be chosen so that these are different enough for the different calibration objects that—at least to a certain extent—deviations in the production of the calibration objects, i.e. in particular in relation to the spacings between their calibration elements, are tolerable, since even with a deviation from the ideal spacings for this calibration object and its double ratio, the actual double ratio deviates less from the ideal double ratio than from the double ratios of the other calibration objects.

In a few advantageous variants the double ratio is a strong descriptor.

In a few forms of embodiment of the method, for which the at least one calibration object or a further calibration object has seven physical calibration elements, of which one lies on a first straight line and on a second straight line, which are not parallel, and of which in each case three further elements are arranged at least essentially along the first or the second straight line, the descriptor on the one hand has an arrangement of four recognized calibration elements at least essentially along a first 2D straight line and also a first double ratio for the spacings between these four calibration elements and on the other hand an arrangement of four recognized calibration elements along a second 2D straight line, which intersects the first 2D straight line in one of these calibration elements, as well as second double ratio for the spacings between these calibration elements. Moreover, during determination of the subsets, those subsets are determined that have seven recognized calibration elements, of which four are arranged along a first 2D straight line and four along a second 3D straight line in the 2D transmission image. Moreover in the method the descriptor for each subset is further computed by way of the first double ratio for the spacings of the four recognized calibration elements along the first 2D straight line and by way of the double ratio for the spacings of the four calibration elements along the second 2D straight line. In particular a sequence of the calibration elements can advantageously be defined by the calibration element at the intersection point of the two straight lines.

In a few advantageous variants with a descriptor that has a number of items of information, a first part of this information can be given implicitly. In this case, in a few advantageous variants, a second part of the information of the descriptor can depend on the presence of the first part or be required in order to determine the second part. In this way the double ratio is in particular defined when the calibration elements are arranged along a straight line. Thus, in a few advantageous variants, the double ratio is determined as a descriptor as a function of the calibration elements being arranged along a straight line.

In a few forms of embodiment the double ratio can be determined in the three dimensional, i.e. in particular for the 3D calibration phantom and for its physical calibration elements, as follows:

Let the vectors of the four calibration elements arranged along a straight line be given as: a, b, c and d.

The following is thus produced as a unit vector along the straight line $$i = \frac{a-b}{\|a-b\|} \in \mathbb{R}^3$$

and as (relative) spacings along the straight line $$a \stackrel{\text{def}}{=} 1 \in R$$

$$b \stackrel{\text{def}}{=} 0 \in R$$

$$c \stackrel{\text{def}}{=} i^T(c-b) \in R$$

$$d \stackrel{\text{def}}{=} i^T(d-b) \in R$$

and as the double ratio $$\lambda = cr(a, b; c, d) \stackrel{\text{def}}{=} \frac{(a-c)\cdot(b-d)}{(a-d)\cdot(b-c)} \in R.$$

In the two dimensional, the double ratio can be determined in a corresponding way. In this case the value of the double ratio for the physical calibration elements determined in the three dimensional corresponds to the value determined in the two dimensional for the corresponding calibration elements recognized in the 2D transmission image, since the double ratio is projectively invariant.

In a few forms of embodiment, the value of the double ratio can depend on the order of the calibration elements—i.e. in particular on which of the calibration elements is assigned the vector a etc. . . . . . Thus, with four calibration elements, six permutations and accordingly six values, namely $$\lambda, \frac{1}{\lambda}, 1-\lambda, \frac{1}{1-\lambda}, \frac{\lambda-1}{\lambda}, \frac{\lambda}{\lambda-1}$$

can be produced. In a few advantageous variants all six values are computed for determining the assignment data.

In a few forms of embodiment, the method can further feature a definition of an order of the calibration elements for each subset by way of a predetermined criterion for the order. In this advantageous way the recognized calibration elements of the subset that is assigned to the at least one calibration object, can each be uniquely assigned to their respective physical calibration element.

In a few advantageous variants, the predetermined criterion for the order can be an intersection point of two straight lines, along which the calibration elements of the at least one calibration object are arranged.

In a few forms of embodiment, in which in the method an order of the calibration elements is defined, the descriptor can feature this order. In this advantageous way the descriptor features further information, which makes possible a distinction between two calibration objects, even if the objects, except for their order—at least in relation to the information of the descriptor—are at least essentially the same.

As an alternative or in addition, in a few forms of embodiment in which an order of the calibration elements is defined, this order can be used to make further information of the descriptor independent of any given permutation in the order or arrangement of the calibration elements of the respective calibration object. Thus, such as with the double ratio for a calibration object, different values are produced depending on which of the calibration elements of the calibration object is assigned a first, a second, a third or a fourth position, whereby different spacings are produced. The fact that a specific order is defined allows a specific order and thus a specific value of the double ratio to be defined for a specific permutation of the calibration elements or their position, through which the value of this double ratio becomes unique for the calibration object.

In a few forms of embodiment, the at least one calibration object or a further calibration object can feature at least one different calibration object, which differs from the other calibration objects in relation to a distinction criterion. In a few advantageous variants the different calibration element can be distinguished by having a larger or a smaller spatial extent. Also, in a few advantageous variants, the distinction criterion can consist of the different calibration element scattering or absorbing the radiation differently. In this advantageous way the different calibration element can be distinguished from the other calibration elements—i.e. at least from the other calibration elements that are arranged spatially in the vicinity of the different calibration element and thus are embodied similarly, in particular pseudo-affine, in the 2D transmission image on the basis of the distinction criterion.

In a few forms of embodiment, in which in the method an order of the calibration elements is defined and in which the at least one calibration object or a further calibration object features at least one different calibration element, the method further has the following feature. For each recognized calibration element the distinction criterion is determined on the 2D transmission image in each case. For each subset it is determined whether and which of the recognized calibration elements of the respective subset differ relative to the other calibration elements through their respective distinction criterion. In this case it is assumed in particular that the calibration elements of a subset are also arranged spatially at least essentially adjacent to one another.

In this case, in a few advantageous variants, the predetermined criterion for the order can be based on the distinction criterion. As an alternative or in addition, in a few advantageous variants, the descriptor can feature a position of the at least one different calibration element within the order of the calibration elements. In this advantageous way the order of the calibration elements can be defined on the basis of the at least one different calibration element. Also calibration objects with otherwise at least essentially the same properties can be distinguished on the basis of the position of the at least one different calibration element.

In a few forms of embodiment, the 3D calibration phantom features a further calibration object with a predetermined number of physical calibration elements, which are spatially arranged and/or embodied corresponding to the physical calibration elements of the at least one calibration object in such a way that the descriptor differs in relation to the further calibration object from the descriptor in relation to the at least one calibration object.

In a few forms of embodiment of the method, for which the 3D calibration phantom features a further calibration object, the method can be carried out correspondingly for the physical calibration elements of the further calibration object. In this case, provided the predetermined number of physical calibration elements for the at least one calibration object and the further calibration object are the same, the recognized calibration elements of that subset are assigned either the physical calibration elements of the at least one calibration object or the physical calibration elements of the other calibration object depending on whether the computed descriptor for this subset differs less from the descriptor of the at least one calibration object or from the descriptor of the further calibration object. In this advantageous way the 3D calibration phantom can feature further calibration elements and/or further calibration objects, so that overall a greater number of calibration elements is produced, whereby in particular the quality of the geometry calibration can be enhanced.

In a few forms of embodiment, the method further features a provision of the assignment data. In a few advantageous variants the assignment data can be output in this case via a data interface. In this advantageous way the assignment data can be used for determining the geometry calibration and/or checked before the determination of the geometry calibration.

In a few forms of embodiment, the method furthermore has a marker-based 3D/3D registration based on the assignment data. In a few advantageous variants, as an alternative or in addition to the geometry calibration one or more transmission images, in particular of a patient or of an object to be examined, is characterized by way of the 3D calibration phantom. In particular through the projective invariance of the descriptor/of the descriptors (for transmission images from different views) a unique assignment can be made possible on the basis of a 3D registration by the 3D registration. Furthermore, in a few advantageous variants, the calibration objects or elements can be flexibly arranged and in this way can flexibly create different 3D registrations.

Also, in a few forms of embodiment, objects to be examined or parts thereof can be characterized on the basis of the 3D calibration phantom, in particular according to a 3D registration. In this advantageous way the positions of objects and especially advantageously of specific parts of objects can be characterized, whereby in particular finding parts of an object to be examined in the transmission image and/or determining their spatial positions is made possible.

In the sense of at least some embodiments of the invention, the transmission imaging in particular comprises the fluoroscopy.

In a few forms of embodiment in which a fluoroscopy is carried out, a patient or an object to be examined or regions or parts thereof are characterized by way of the 3D calibration phantom, such as advantageously by 3D registration.

In a few forms of embodiment, the method can furthermore feature a calculation in each case of a first error value for each subset, which identifies the deviation between the descriptor computed for this subset and the descriptor of the at least one calibration object or of a further calibration object. Moreover the recognized calibration elements of one of the subsets are assigned physical calibration elements of the at least one or of the further calibration object dependent on whether the respective first error value is smaller than a first limit value.

In a few forms of embodiment, the method is carried out repeatedly with differently determined subsets of the recognized calibration elements. In particular, in a few advantageous variants, a so-called RANSAC algorithm can be executed, so that the method is carried out iteratively and the assignment of the recognized calibration elements to the physical calibration elements is done adaptively and in this case in particular an first error value and/or an overall error value, which comprises the first error values, is minimized.

An advantage of the repeated execution can in particular lie in the fact that errors can be reduced in the assignment, whereby in particular the quality of a subsequent geometry calibration can be improved. An advantage of the adaptive assignment through application of the RANSAC algorithm can in particular lie in the fact that RANSAC is a statistical algorithm, through which, even with errors in the assignment data and/or even with weak descriptors, a correct assignment—i.e. in particular a correct minimum assignment—can be determined at least for a true subset of the recognized calibration elements. Thus, through the application of the RANSAC algorithm in particular, the robustness of the method can be enhanced. Also, in a few advantageous variants, the geometry calibration can already be carried out based on such a minimal assignment.

A second embodiment of the invention relates to a 3D calibration phantom for determining a geometry calibration and assignment data for an imaging device. In the imaging device, in a transmission imaging, after passing through the 3D calibration phantom, radiation strikes a 2D detector to create a 2D transmission image of the 3D calibration phantom. The 3D calibration phantom has at least one calibration object with a predetermined number of physical calibration elements, which are arranged spatially in such a way that a descriptor based on the spatial arrangement is projectively invariant under the transmission imaging. Overall the 3D calibration phantom has at least seven physical calibration elements. In this case the physical calibration elements feature a material that is opaque for the radiation and/or that absorbs or scatters the radiation.

The possible advantages, forms of embodiment or variants of the first embodiment of the invention already stated previously also apply accordingly for the inventive 3D calibration phantom. In particular through the total of seven physical calibration elements—with a suitable arrangement, i.e. general spatial arrangement, without any coplanarity—allow a geometry calibration, i.e. in particular a projection matrix on the basis of the spatial arrangement of these at least seven physical calibration elements and their two-dimensional mapping in the 2D transmission image, to be advantageously determined.

In a few forms of embodiment the predetermined number of physical calibration elements of the at least one calibration object is four, so that with a collinear arrangement—i.e. along a straight line—the double ratio can be computed as an, in particular, strong descriptor or as part of the descriptor.

In a few forms of embodiment the 3D calibration phantom has a further calibration object with a predetermined number of physical calibration elements, which according to the physical calibration elements of the at least one calibration object are spatially arranged in such a way that and/or according to the physical calibration elements of the at least one calibration object are embodied in such a way that the descriptor in relation to the further calibration object differs from the descriptor in relation to the at least one calibration object. In this advantageous way the two calibration objects and their calibration elements can be distinguished from each other.

In a few advantageous forms of embodiment the at least one calibration object or the further calibration object can be embodied as a pin, in which the calibration elements are permanently molded and are arranged along a straight line.

As an alternative or in addition the at least one calibration object or the further calibration object in a few forms of embodiment can be embodied as a holder device for the calibration elements, so that the calibration elements can be arranged in different spatial positions, in particular along a straight line.

Accordingly, in a few forms of embodiment the individual calibration objects—i.e. in particular the at least one calibration object and/or the further calibration object—can be permanently cast into a shape of the 3D calibration phantom or the 3D calibration phantom can be embodied as a flexible frame, so that the calibration objects can be arranged flexibly on this frame. In such cases a permanent casting-in advantageously increases the robustness of the 3D calibration phantom, while an embodiment as a frame makes a more flexible application possible.

In a few forms of embodiment, in which the calibration objects or at least a few of the objects have four calibration elements arranged along a straight line, the 3D calibration phantom has at least three such calibration objects—in particular pins. In this advantageous way a geometry calibration can already be determined, provided the calibration elements of the calibration objects are not/will not be arranged coplanarly. Thus in particular only a small overall number of calibration elements is needed for the geometry calibration.

In particular through the use of pins as calibration objects and/or through the use of a flexible frame as a 3D calibration phantom, the shape, size and/or number of calibration elements of the 3D calibration phantom can be adapted to the respective object to be examined, for which a geometric calibration is to be carried out. In this case the calibration objects might be arranged along a long cylinder for a spiral trajectory, which is intended to accept a long object. Also the spatial extension of the calibration phantom can be adapted by corresponding arrangement of its calibration objects on the size of the object to be examined, so that for a large object the calibration objects are widely spaced from one another and for an object to be examined the calibration objects are arranged close to one another. The quality of the determination of the data for the geometry calibration can also be further enhanced by the calibration phantom having further calibration objects or further calibration elements, which do not necessarily have to be assigned to a calibration object and according to a descriptor. Also such a 3D calibration phantom allows the quality of the determination of the data for the geometry calibration to be enhanced for a given direction and/or independent of a preferred direction.

Also calibration objects with a small predetermined number of calibration elements, such as less than 50, less than 30, less than 20, less than 15 or not more than seven, can be produced more easily and/or with greater precision than a calibration object or a calibration phantom with more than these calibration elements.

A third embodiment of the invention relates to a method for determining a geometry calibration for an imaging device. In the imaging device, in a transmission imaging, after passing through a 3D calibration phantom, radiation strikes a 2D detector for creating a 2D transmission image of the 3D calibration phantom. In this case the 3D calibration phantom is embodied according to the second embodiment of the invention.

The method of this embodiment has the following features. The 2D transmission image, in which the at least one calibration object of the 3D calibration phantoms is represented, is provided. By the method in accordance with the first embodiment of the invention calibration elements are recognized in the 2D transmission image and assigned to the physical calibration elements of the 3D calibration phantom. Moreover in the method 3D arrangement data is provided for the geometry calibration, which characterize the 3D arrangement of the physical calibration elements. Finally projection data of the geometry calibration, in particular a projection matrix, is determined for the 2D transmission image on the basis of the 3D arrangement data, on the basis of the calibration elements assigned to the physical calibration elements and recognized in the 2D transmission image and on the basis of the 2D arrangement of the recognized calibration elements.

The possible advantages, forms of embodiment or variants of the preceding aspects of the invention already stated above also apply accordingly for the inventive method for determining a geometry calibration.

In a few forms of embodiment the 3D arrangement data is provided by the data being predetermined and being received from a data storage device for the 3D arrangement data in relation to the 3D calibration phantom. In this advantageous way, with predetermined, i.e. in particular 3D, arrangement data previously known and/or physically measured before or as part of the method for the calibration phantom used, the determination of the projection data and thus the determination of the geometry calibration can be efficiently carried out and/or already be carried out when only a 2D transmission image is present.

In a few forms of embodiment, in particular in those with unknown 3D arrangement data, the geometry calibration features the 3D arrangement data and the projection data. To determine the geometry calibration, one or more additional 2D transmission images relating to additional views of the 3D calibration phantom are provided. Moreover, by way of a method in accordance with the first embodiment of the invention, calibration elements recognized in each case in the additional 2D transmission images are assigned to the physical calibration elements of the 3D calibration phantom. Finally the—in particular initially unknown—3D arrangement data is provided and the respective projection data of the geometry calibration is determined for each 2D transmission image, by the 3D arrangement data being modeled such that, with this 3D arrangement data, the differences between the computed descriptors for the recognized calibration elements of the respective subsets of the respective 2D transmission images from the corresponding descriptors of the physical calibration elements are minimized.

In this advantageous way the geometry calibration—thus in particular the 3D arrangement data and the projection data, in particular the projection matrices—can be determined, without the 3D arrangement data having to be known. This in particular allows the quality of the geometry calibration to be enhanced, since this can be carried out independently of a preceding and possibly faulty (in particular physical) measurement of the 3D arrangement of the calibration elements. Also, in this advantageous way, the determination of the geometry calibration can be simplified and/or designed more flexibly, since it is not a matter of an exact, previously known spatial arrangement of the calibration elements. Instead calibration elements of the 3D calibration phantom can be spatially arranged in the method before carrying out the method or its start—in particular depending on the objects to be examined, wherein the exact spatial arrangement—and thus the 3D arrangement data—are determined in the method.

In a few forms of embodiment, the method features a determination of a second error value, which characterizes the difference in each case between the 2D arrangement of one of the recognized calibration elements in the respective 2D transmission image and the 2D arrangement computed on the basis of the 3D arrangement data via the projection data. In this case, in a few advantageous variants, the quality of the geometry calibration can be quantified by way of the second error values.

In a few forms of embodiment with first and second error values, the overall error is computed on the basis of the first error values and the second error values, in particular as the sum of their absolute amounts.

In a few forms of embodiment, in which first or second error values and/or an overall value are computed, the method is carried out iteratively, in order to minimize at least one of these error values. In a few advantageous variants the method can be implemented as a RANSAC algorithm, so that in particular the respective error is minimized.

In a few forms of embodiment, for determining the geometry calibration iteratively, an Iterative Closest Point algorithm (ICP algorithm) followed by a non-linear minimization of the Euclidian back projection error—in particular a so-called bundle adjustment—is carried out. In this way the geometry calibration can be determined with especially high quality—i.e. in particular with especially high accuracy, wherein in particular, for an efficient implementation, there can also be recourse to the experiences in computer vision with these types of algorithm.

In a few forms of embodiment, for determining the geometry calibration, initially iteratively as a first step the RANSAC algorithm and subsequently as the second step a non-linear minimization of the Euclidian back projection error—in particular a so-called bundle adjustment—is carried out. In this way the geometry calibration can be determined initially robustly and then with especially high quality, wherein in particular for an efficient implementation and/or a high robustness, there can also be recourse to the experiences in computer vision with these types of algorithms.

In a few forms of embodiment, the calibration elements recognized in the 2D transmission are assigned to one another between at least one first and one second 2D transmission image by way of an automatic calculation of the epipolar geometry. In this advantageous way the quality of the geometry calibration can be enhanced and/or the efficiency in their determination, i.e. in particular the computing power and/or computing time needed therefor can be reduced.

A fourth embodiment of the invention relates to a device for determining a geometry calibration for an imaging device. In the imaging device, in a transmission imaging, after passing through a 3D calibration phantom, radiation strikes a 2D detector to create a 2D transmission image of the 3D calibration phantom. In this case the 3D calibration phantom is embodied in accordance with the second embodiment of the invention. The device has a data processing device and a data interface. In this case the data interface is configured to receive 2D transmission images from the imaging device. Finally the device is configured to carry out a method in accordance with the third embodiment of the invention.

The possible advantages, forms of embodiment or variants of the aspects of the invention already mentioned previously also apply correspondingly for the inventive device for determining a geometry calibration.

A further embodiment of the invention relates to a calibratable, imaging system, which features a device in accordance with the fourth embodiment of the invention and features an imaging device. In this case, in a few variants, the imaging device can be embodied as a computed tomography system or as the imaging part of a computed tomography system and/or the system can be embodied as the computed tomography system, which is configured to carry out a method in accordance with the third embodiment of the invention.

The possible advantages, forms of embodiment or variants of the preceding aspects of the invention already stated above also apply accordingly for the calibratable imaging system in accordance with a further aspect of the invention.

A 3D calibration phantom 10 according to a form of embodiment of the present invention is shown schematically in FIG. 1.

In an example embodiment the 3D calibration phantom 10 has a number of calibration objects 100, 110, 120—i.e. a minimum of at least one calibration object 100 and a further calibration object 110 and/or a total of three calibration objects. Each of the calibration objects 100, 110, 120 has four physical calibration elements 102, 104, 106, 108 or 112, 114, 116, 118 or 122, 124, 126, 128 in each case, which are arranged spatially in each case along a straight line, as well as a holder device 101, or 111, or 121 in each case.

Advantageously, in a few variants, the calibration objects are arranged skewed in relation to one another with regard to the straight line, along which their respective calibration elements are arranged spatially.

The physical calibration elements 102, 104, 106, 108, 112, 114, 116, 118, 122, 124, 126, 128 feature a material that scatters a radiation for a transmission imaging, or are in particular manufactured from this material. The holder devices 101, 111, 121 are manufactured with one or with a number of materials so that these at least do not essentially disturb the scattering of the radiation by the physical calibration elements, when the physical calibration elements are held by the respective holder device. In particular the holder devices can be manufactured for this purpose from a material that at least essentially does not scatter the radiation.

In a few variants the holder devices 101, 111, 121 can be manufactured from a plastic through which the radiation can pass and in particular can consist thereof and also the physical calibration elements can be manufactured from a metal or a mixture of a metal and a plastic or can consist thereof, so that the radiation is scattered.

As shown in FIG. 1, each of the physical calibration elements 108, 114, 122 differs from the other physical calibration elements of the calibration objects 100, 110, 120. In this case these calibration elements 108, 114, 122 are distinguished in such a way that they scatter or absorb the radiation in other ways compared to the other physical calibration elements, such as in particular scatter it less. For this purpose, in physical calibration elements manufactured from a mixture of a metal and a plastic, in a few variants for the calibration elements with lower scattering 108, 114, 122 a lower proportion of metal and a higher proportion of plastic can be used in the mixture ratio.

In a few variants, in addition or as an alternative, the size of the physical calibration elements can be varied and for instance for calibration elements with lower scattering or absorption a smaller size, i.e. a smaller spatial extent, can be used. Conversely, for instance for calibration elements with greater scattering or absorption, a larger size, i.e. a greater spatial extent can be used.

In a few variants the holder devices 101, 111, 121 are embodied as a cylinder or half cylinder and have at least four receiving areas in each case, each for one of the four physical calibration elements of the respective calibration object.

In a few advantageous variants and as shown in FIG. 1, the different calibration element 108, 114, 122 compared to the other calibration elements can be positioned at a first, a second, a third (not shown) or a fourth position in relation to the order of the physical calibration elements in their spatial arrangement along the respective straight line. In this way the calibration objects 100, 110 for instance have at least essentially the same spacings between their calibration elements, i.e. the spacing between the calibration element 102 and the calibration element 104 corresponds to the spacing between the calibration elements 112 and 114, the spacing between the calibration elements 102 and 106 corresponds to the spacing between the calibration elements 112 and 116 as well as the spacing between the calibration elements 102 and 108 corresponds to the spacing between the calibration elements 112 and 118, however the two calibration objects 100, 110 differ in that the calibration element 108 of the calibration object 100 is arranged at the fourth position and the calibration element 114 of the calibration object 110 is arranged at the second position. In this way calibration objects that are otherwise at least essentially the same can be distinguished from one another and/or an order of the calibration elements of the respective calibration object can be defined.

A further possibility for distinguishing between calibration objects is a different spatial arrangement, i.e. in particular different spatial distances between their respective calibration elements. Thus for instance the calibration elements of the calibration object 120 have the same spacings from one another, while the spacings between calibration elements of the calibration object 100 are different.

The double ratio based on the spacings of the respective calibration elements from one another can be determined as the descriptor for the respective calibration object 100, 110, 120, in particular through the arrangement of each of the four calibration elements along a straight line. In this case the respective descriptor can in particular have further features, in particular the order of the calibration elements and/or the arrangement of the calibration elements along a straight line.

This double ratio is projectively invariant for a transmission imaging via an imaging device, in which, after passing through the 3D calibration phantom 10, radiation strikes a 2D detector for creating a 2D transmission image of the 3D calibration phantom 10. Such a transmission imaging can have different transformations as regards the mapping of the respective three-dimensional object, i.e. here in particular of the 3D calibration phantom to the 2D transmission image, in particular a rigid transformation, a similarity transformation, an affine transformation, a pseudo affine transformation or in general a projective transformation. An advantage of the use of the double ratio as descriptor or as part of the descriptor can thus in particular lie in the fact that this double ratio is projectively invariant as regards the transformations, so that this can be determined independently of the respective concrete transformation in the transmission imaging and in such cases delivers a value that remains the same—i.e. is invariant, whereby the respective calibration object is able to be identified via its descriptor, i.e. in particular via the respective value of the double ratio for this calibration object. Accordingly the calibration elements of a calibration object identified in this way can be assigned to its respective mappings in the 2D transmission image and/or vice versa, wherein it can be necessary, in a few variants, to define the order of the calibration elements of the respective calibration object and advantageously determine it for these calibration elements, such as by way of a distinction criterion.

Figure 2:
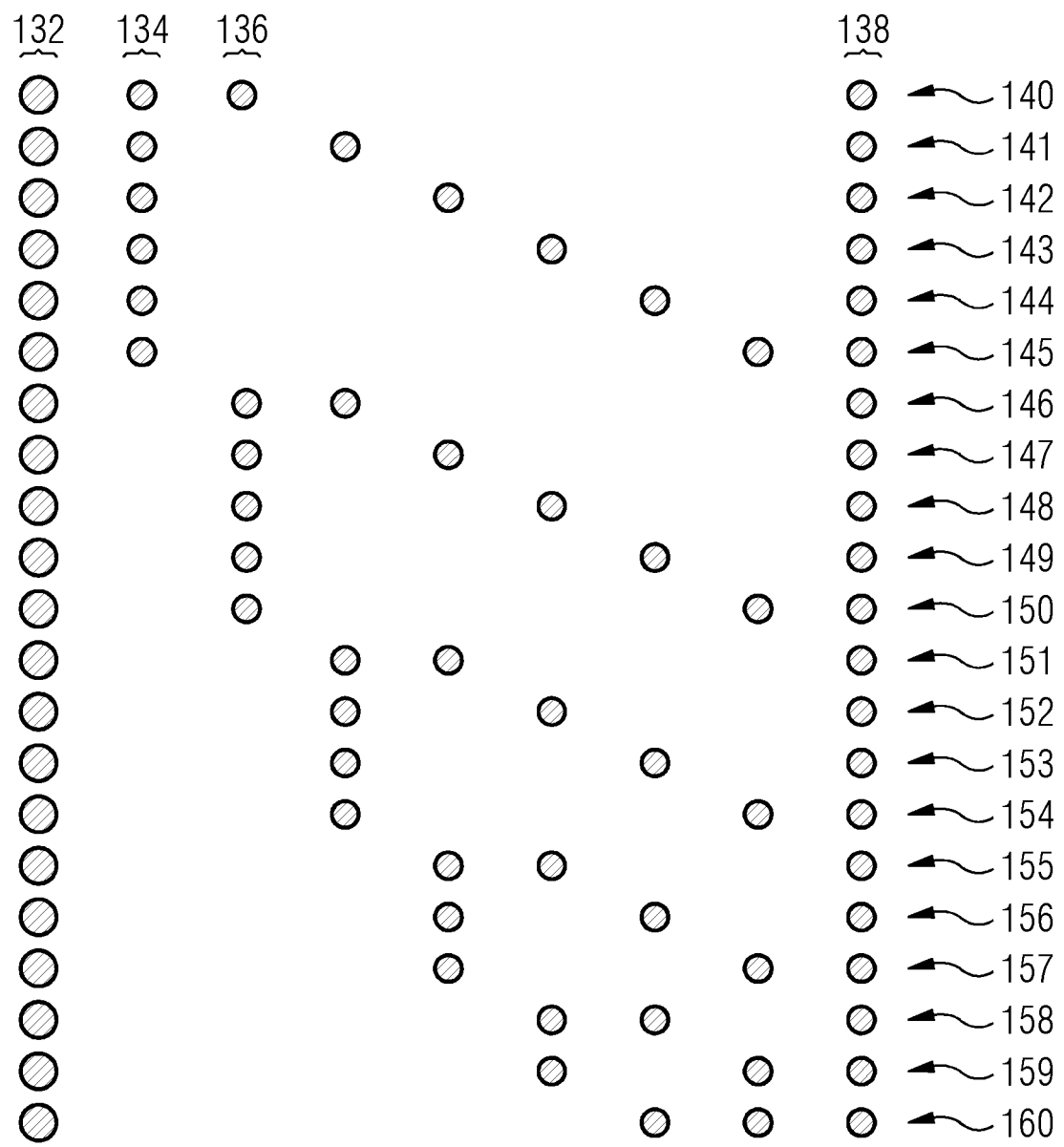
FIG. 2: shows a number of calibration objects for a 3D calibration phantom according to a form of embodiment.

FIG. 2 shows a schematic diagram of a number of calibration objects 140, 141, 142, . . . 160 according to a number of forms of embodiment for a 3D calibration phantom according to a form of embodiment of the present invention.

In an example embodiment the calibration objects 140-160 each have four calibration elements 132, 134, 136, 138. The calibration elements 132, 134, 136, 138 consist at least essentially of a material that absorbs the radiation. Moreover the spatial extent of the respective calibration element 132 (for the respective calibration object 140-160) has a greater spatial extent than the other calibration elements 134, 136, 138. If in FIG. 2 the calibration elements for the respective calibration object are viewed from left to right, then the calibration element 132, which differs by its spatial extent, is arranged at a first position.

Figure 3:
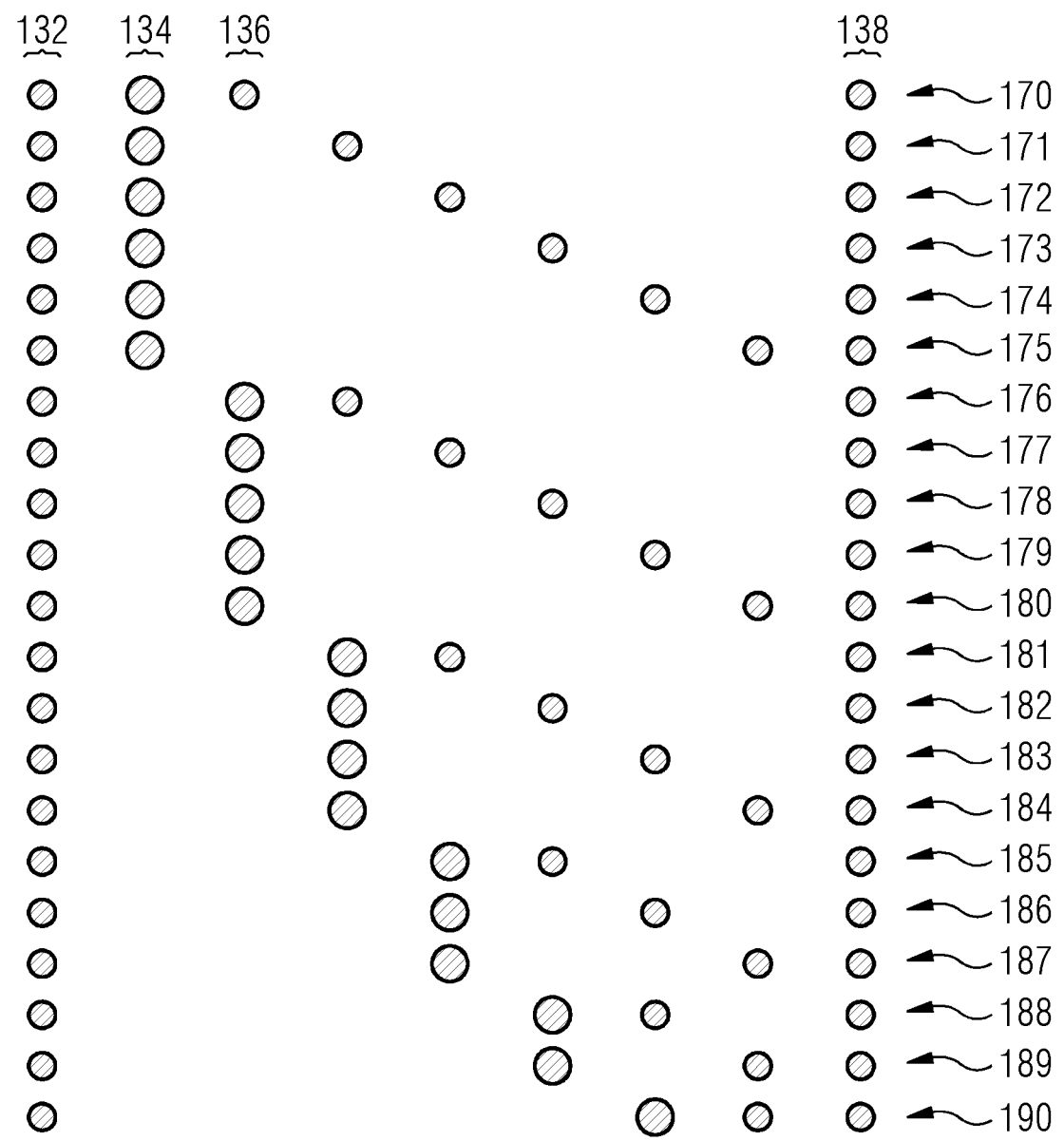
FIG. 3: shows further calibration objects for a 3D calibration phantom according to a form of embodiment.

Accordingly FIG. 3 shows further calibration objects 170, 171, . . . 190 according to a number of forms of embodiment for a 3D calibration phantom according to a form of embodiment of the present invention.

These calibration objects 170-190 also each have four calibration elements 132, 134, 136, 138 in an example embodiment. The calibration objects from FIG. 3 differ from the calibration objects from FIG. 2, in that the respective calibration element 134 in FIG. 3 is different compared to the calibration elements 132, 136, 138, in particular has a greater spatial extent, and this respective calibration element 134 is arranged at second position.

With a descriptor, in particular a double ratio, this difference between the calibration objects from FIG. 2 and FIG. 3 can be characterized in that the double ratio for calibration objects with the different calibration element in first position is positive and the double ratio for calibration objects with the different calibration element in second position is encoded with a negative value.

For the calibration objects shown in FIG. 2, the following is produced as an encoded value for the double ratio for the descriptor:

| Calibration object | Double ratio |
| --- | --- |
| 140 | 2 |
| 141 | 4 |
| 142 | 7 |
| 143 | 11 |
| 144 | 21 |
| 145 | 49 |
| 146 | 1 |
| 147 | 3 |
| 148 | 5 |
| 149 | 9 |
| 150 | 21 |
| 151 | 1 |
| 152 | 2 |
| 153 | 5 |
| 154 | 11 |
| 155 | 1 |
| 156 | 3 |
| 157 | 7 |
| 158 | 1 |
| 159 | 4 |
| 160 | 2 |

For the calibration objects shown in FIG. 3, the following is produced as an encoded value for the double ratio for the descriptor:

| Calibration object | Double ratio |
| --- | --- |
| 170 | −2 |
| 171 | −4 |
| 172 | −7 |
| 173 | −11 |
| 174 | −21 |
| 175 | −49 |
| 176 | −1 |
| 177 | −3 |
| 178 | −5 |
| 179 | −9 |
| 180 | −21 |
| 181 | −1 |
| 182 | −2 |
| 183 | −5 |
| 184 | −11 |
| 185 | −1 |
| 186 | −3 |
| 187 | −7 |
| 188 | −1 |
| 189 | −4 |
| 190 | −2 |

Advantageously in this case, in a few variants, a 3D calibration phantom has such calibration objects as differ in the value of their double ratio at least as regards their leading sign, so that the individual calibration objects in particular can be uniquely assigned on the basis of their descriptor, thus in particular a strong descriptor is present.

Figure 4:
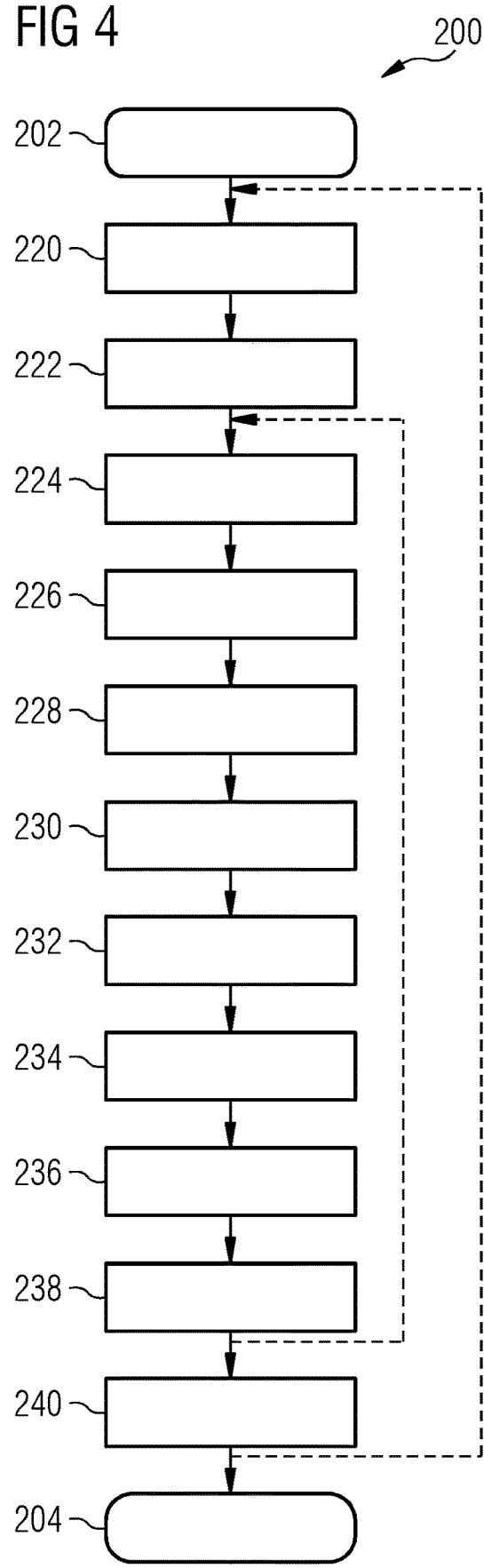
FIG. 4: shows a flow diagram of a method for determination of assignment data for an imaging device according to a form of embodiment.

Shown in FIG. 4 is a flow diagram of a method 200 for determining assignment data for an imaging device according to a form of embodiment of the present invention. In such an imaging device, for creating a 2D transmission image of a 3D calibration phantom in a transmission imaging, after passing through the 3D calibration phantom, radiation strikes a 2D detector. In this case the 3D calibration phantom is embodied in accordance with a form of embodiment of the present invention and can in particular correspond to one of the calibration phantoms in accordance with FIG. 1, 2 or 3.

In an example embodiment the method 200 has the method steps 220, 222, 224, 226, 228, 230, 232, 234, 236, 238 and 240. The method 200 begins at the method start 202 and ends at the method end 204, wherein one or more method steps, in particular a sequence of method steps, and preferably the entire method can be carried out repeatedly.

In method step 220 the 2D transmission image, in which the at least one calibration object of the 3D phantom is mapped, is provided.

In method step 222, for determining calibration elements recognized in the 2D transmission image and their 2D arrangement, the physical calibration elements mapped in the 2D transmission image are recognized.

In a few variants the calibration elements can be embodied as spheres or pearls. Also, in a few variants, the physical calibration elements mapped in the 2D transmission image, in particular when they are sphere-shaped or pearl-shaped, can be detected by way of a so-called "blob detector". In this case, in a few variants, the spatial, or in the 2D transmission image the two-dimensional extent of the respective recognized calibration element, can be determined as a distinction criterion, in particular by way of such a "blob detector".

In a few variants, in which the at least one calibration object of the 3D calibration phantom has a calibration element with a greater spatial extent, the spatial extent or the two-dimensional extent in the 2D transmission image—at least relative to other calibration elements of at least the same subset—has a so-called "Fast Radial Symmetry Transform", which is applied twice, and a removal of calibration elements, which have too small an extent and/or lie too close to other calibration elements, the 2D arrangement of the calibration elements with larger extent and of the calibration elements with smaller extent is determined.

In method step 224 subsets of the recognized calibration elements are determined in such a way that the number of calibration elements in the subsets corresponds in each case to the predetermined number of physical calibration elements of the at least one calibration object. In particular for calibration objects, of which calibration elements are arranged along a straight line, subsets can furthermore be determined in this case so that the recognized calibration elements of one of the subsets are also arranged in the 2D transmission image along a straight line.

In method step 226 the descriptor is computed in each case in relation to the calibration elements for each subset. In a few variants, in which the calibration elements of the at least one calibration object are arranged along a straight line and the calibration object has at least four and in particular exactly four calibration elements, the descriptor or a part thereof can be determined via the double ratio, as described above.

Since the double ratio can depend in particular on the order of the calibration elements within the respective subset in each case—i.e. in particular different values for the double ratio are produced for different permutations within a subset—it can be advantageous to define the order of the calibration elements by way of a distinction criterion for the individual calibration elements of the at least one calibration object.

In a few variants, in particular in order to define the order of the calibration elements, in method step 228 the extent of the calibration elements is determined as the distinction criterion on the 2D transmission image for each recognized calibration element.

In method step 230, based thereon, those calibration elements are determined that differ compared to the usual calibration elements of this subset by having a greater extent.

In method step 232 the order of the calibration elements for each subset is defined by way of the distinction criterion, i.e. in particular by way of the extent in the 2D transmission image, so that the respective subset might for instance be arranged so that, with an outer location of the recognized calibration element, which because of its extent, differs from the others of this subset, this calibration element is in first position and this different calibration element, when it is in an inner location—i.e. other calibration elements along the straight line lie even further outwards—is in second position. In this case, in a few variants, a pseudo-affine mapping of the 3D calibration phantom to the 2D transmission image is assumed, so that in particular the arrangement or order remains preserved along a straight line during the mapping.

As an alternative or in addition for defining the order, further previously known data can be used for uniquely determining the descriptor or the method can be applied iteratively, so that in particular any descriptors are determined for all possible permutations or at least for a significant part of the permutations.

In a few variants in method step 234 the descriptors of the (physical) calibration objects are provided, by the descriptors being received from a data storage device. As an alternative or in addition, in a few variants, these descriptors can be determined by an iterative execution of the method within the framework of an optimization—such as by way of a RANSAC algorithm.

In method step 236 a first error value is computed in each case for each subset, which characterizes the deviation between the descriptor computed for this subset and the descriptor of the at least one calibration object. In a few variants, in which the method is executed iteratively, an overall error of this first error is formed in this case and this is optimized for the at least one calibration object and further calibration objects and/or for the 2D transmission image and further transmission images.

In method step 238 the assignment data is determined by the recognized calibration elements of one of the subsets being assigned to the physical calibration elements of the at least one calibration object, depending on whether the respective first error value is less than a first limit value. In a few variants in this case this first limit value can be predetermined. As an alternative or in addition, in a few variants, this first limit value can be dynamic and be dependent on the first error values in relation to the subsets, so that in particular with a number of calibration objects, the arrangement of the calibration elements is optimized and in this way in particular the overall error, which is based on the first error values, is minimized.

Such an iterative optimization can advantageously be carried out in a few variants by way of the so-called RANSAC algorithm, wherein in particular the method steps 224-236 and in particular when a number of 2D transmission images are used, also the method step 238 is repeated and for various specific subsets is carried out iteratively, in particular until an overall error lies below a predetermined limit value for the overall error or a specific number of iterations have been carried out or statistically no significantly lower overall error is to be expected for further iterations.

Finally, in method step 240, the assignment data is provided. In a few variants the assignment data can be output in this case via a data interface.

An advantage of this method and of the assignment data determined in this way can in particular lie in the fact that the calibration elements recognized in the 2D image can be assigned to the physical calibration elements of the at least one calibration object, whereby in particular the so-called correspondence problem can be solved and with which algorithms can be transferred to the transmission imaging from computer vision for determining mapping properties and/or projection properties and in this way in particular can be used for determining the geometry calibration.

Figure 5:
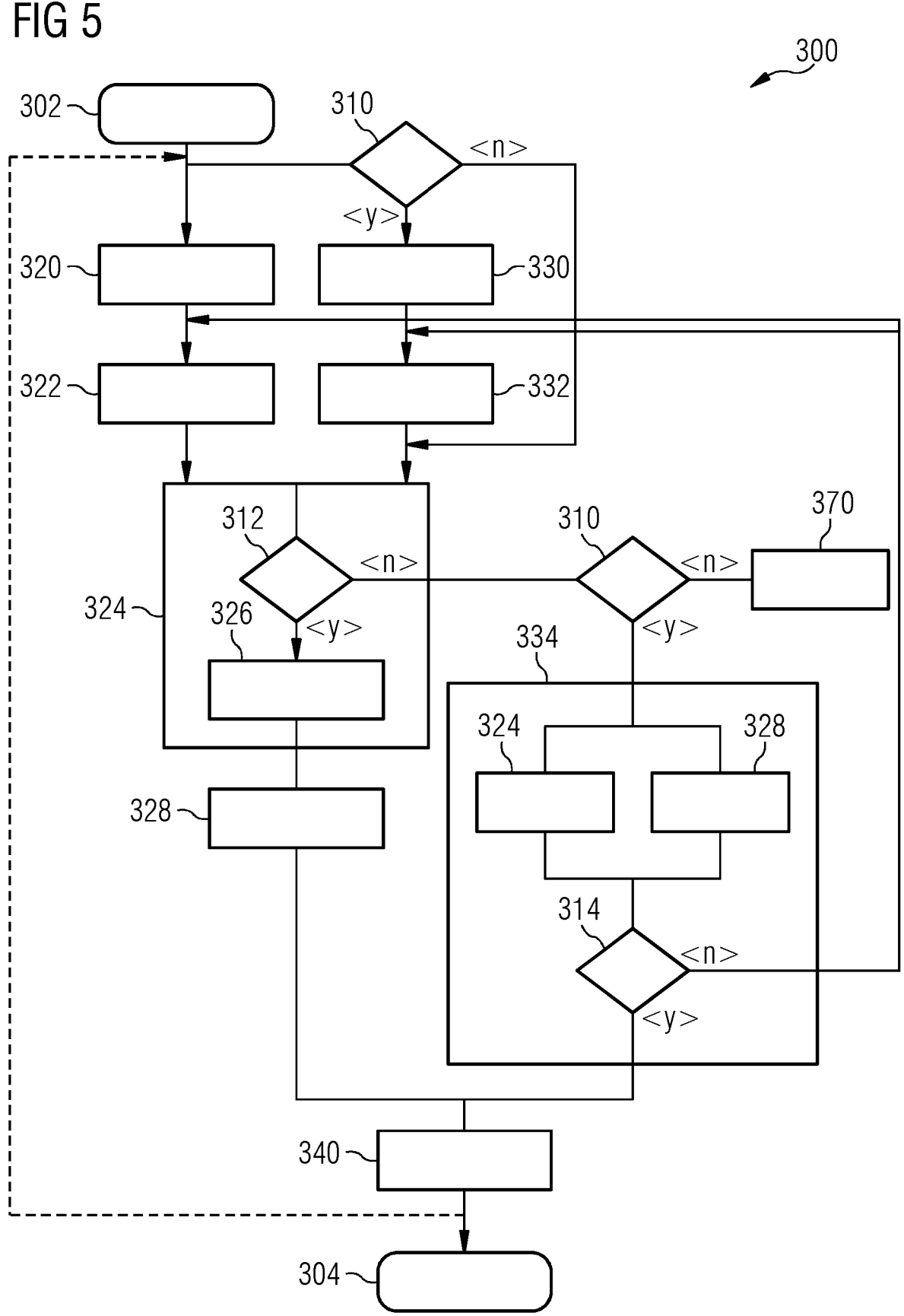
FIG. 5: shows a flow diagram of a method for determination of a geometry calibration for an imaging device according to a form of embodiment.

Shown in FIG. 5 is a flow diagram of a method 300 for determining a geometry calibration for an imaging device according to a form of embodiment of the present invention. In the imaging device, in a transmission imaging, after passing through a 3D calibration phantom, which is embodied in accordance with a form of embodiment of the 3D calibration phantom of the present invention and in particular in accordance with a form of embodiment relating to the preceding figures, radiation strikes a 2D detector for creating a 2D transmission image of the 3D calibration phantom.

In an example embodiment the method 300 has the method steps 320, 322, 324, 326, 328, 330, 332, 334, 340 and 370 and also the method conditions 310, 312 and 314. The method 300 begins in the method start 302 and ends in the method end 304, wherein one or more method steps, in particular a sequence of method steps, and preferably the entire method can be carried out repeatedly.

In method step 320 the 2D transmission image, in which the at least one calibration object of the 3D calibration phantom is shown, is provided.

In method step 322 a method for determining assignment data according to a form of embodiment of the present invention and in particular according to a form of embodiment in relation to FIG. 4 is carried out, in order to recognize calibration elements in the 2D transmission image and to assign the physical calibration elements of the 3D calibration phantom.

In the method condition 310 a check is made as to whether the method is to be carried out for a 2D transmission image, or whether the method is also to be carried out for additional 2D transmission images.

If this is the case, which is indicated by the symbol <y> in the flow diagram, in method step 330 one or more additional 2D transmission images in relation to additional views of the 3D calibration phantom are provided. Moreover, in method step 332 the physical calibration elements of the 3D calibration phantom are assigned calibration elements recognized in each case in the respective additional 2D transmission images according to the method start 322.

If this is not the case—i.e. the method is only to be carried out for the one 2D transmission image, which is indicated in FIG. 5 by the symbol <n>t—the method steps 330 and 332 are not carried out.

In method step 324 3D arrangement data for the geometry calibration, which characterizes the 3D arrangement of the physical calibration elements, is provided. In this case a distinction is made in accordance with method conditions 312 as to whether the 3D arrangement data is known in advance and/or stored.

If this is the case, the 3D arrangement data is received in method step 326 from a data storage device for the 3D arrangement data relating to the 3D calibration phantom. If this is not the case—indicated by the symbol <n>—a check is made with the method conditions 310 as to whether additional 2D transmission images are present. If this is not the case, an error signal is output in method step 370, which indicates insufficient data, after which the method can in particular be stopped or ended or can be carried out again—for instance with further data/2D transmission images.

If additional 2D transmission images are present, the method step 334 is carried out.

In method step 334 the 3D arrangement data is provided in parallel in accordance with an alternate method step 324 and the projection data is determined in accordance with an alternate method step 328, by the 3D arrangement data being modeled so that, with this 3D arrangement data, the differences between the computed descriptor for the recognized calibration elements of the respective subsets of the respective 2D transmission images and the corresponding descriptors of the physical calibration elements are minimized, wherein in the method condition 314, a check is made as to whether a sufficient minimization is present, and, if this is not the case, the method steps as from method step 322 and also the method steps as from method step 332 are carried out again.

In a few variants this type of minimization can advantageously be carried out by way of the RANSAC algorithm.

An advantage of such an iterative method can in particular lie in the fact that the 3D arrangement of the calibration elements of the 3D calibration phantom does not have to be known in advance, but can be determined by the iterative method itself. In this advantageous way an enhanced accuracy can be achieved and/or a dependency on the previously known values and data for the 3D arrangement of the calibration elements, which itself can be susceptible to an uncertainty, is avoided. For further determination of the geometry calibration, i.e. in particular of the 3D arrangement data, the assignment between the calibration elements of the 3D calibration phantom and of the recognized calibration elements in the 2D transmission images as well as corresponding projection matrices, further data, in particular a scaling factor, can be provided.

Provided the 3D arrangement data is known in advance, i.e. method condition 312 is fulfilled, after method step 326 in method step 328 the projection data of the geometry calibration, i.e. in particular a projection matrix, is determined for the 2D transmission image on the basis of the 3D arrangement data, of the calibration elements assigned to the physical calibration elements and recognized in the 2D transmission image and the 2D arrangement of the recognized calibration elements. Here, in a few variants, the method can likewise be carried out repeatedly for optimization. In this case however the 3D arrangement data does not have to be determined, so that a faster convergence can be achieved.

Finally, in method step 340, data relating to the geometry calibration determined by way of this method, i.e. in particular a projection matrix for each 2D transmission image, is output via a data interface. On the basis of this geometry calibration, from 2D transmission images of an object to be examined three-dimensional data relating to this object to be examined can be reconstructed, wherein in particular mapping errors of the respective imaging device can be computed out.

Figure 6:
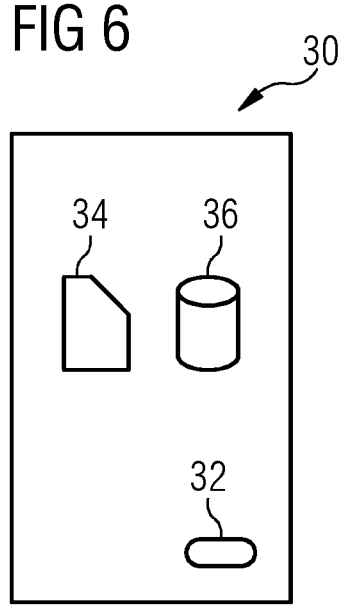
FIG. 6: shows a device for determination of a geometry calibration for an imaging device according to a form of embodiment.

FIG. 6 shows a schematic of a device 30 for determining a geometry calibration for an imaging device, in which in a transmission imaging, after passing through a 3D calibration phantom, radiation strikes a 2D detector for creating a 2D transmission image of the 3D calibration phantom, according to a form of embodiment of the present invention. In this case the 3D calibration phantom is embodied in accordance with a form of embodiment of the present invention and in particular in accordance with a form of embodiment relating to one of FIGS. 1, 2 and 3.

In an example embodiment the device 30 has a data processing device 34, a data storage device 36 and a data interface 32. In this case the data interface 32 is configured for receiving 2D transmission images from the imaging device. Moreover the device 30 is configured for carrying out a method for determining a geometry calibration for an imaging device in accordance with a form of embodiment of the present invention and in particular in accordance with a form of embodiment relating to FIG. 5.

Figure 7:
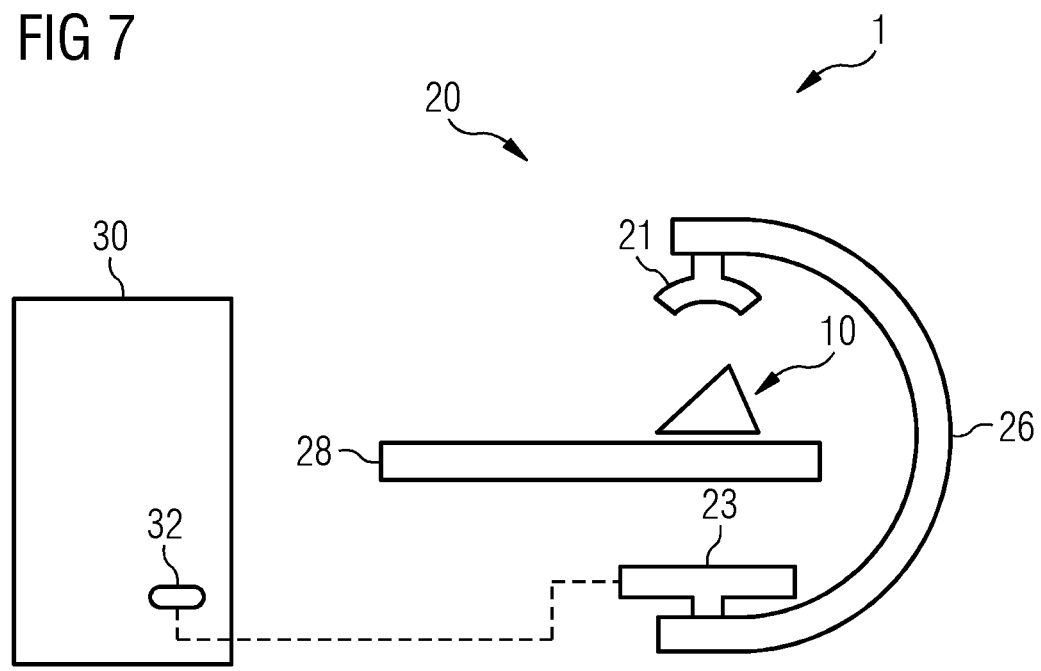
FIG. 7: shows a calibratable imaging system according to a form of embodiment.

Shown schematically in FIG. 7 is a calibratable imaging system according to a form of embodiment of the present invention.

In an example embodiment, the system 1 has an imaging device 20 and a device 30 for determining the geometry calibration. The device 30 for determining the geometry calibration is embodied in accordance with a form of embodiment of the present invention and in particular in accordance with a form of embodiment relating to FIG. 6. In a few variants the imaging device 20 can be embodied as a computed tomography device.

In a few variants, the system 1 can also have a 3D calibration phantom 10 in accordance with a form of embodiment of the present invention and in particular in accordance with a form of embodiment relating to FIGS. 1, 2, 3. In other variants the system 1 can have no 3D calibration phantom 10, but can be configured, after provision of the 3D calibration phantom 10, to record one or more 2D transmission images of the 3D calibration phantom.

In an example embodiment the imaging device 20 has a radiation source 21 for creating a radiation and a 2D detector 23. In this case the radiation source 21 and the 2D detector 23 can be arranged along a holder device 26—in particular embodied as a so-called C-arm. Moreover a 3D calibration phantom 10 can be arranged on a carrier device 28—such as a table. When a transmission imaging is carried out via the imaging device 20 a 2D transmission image of the 3D calibration phantom 10 is created, in that the radiation from the radiation source 21, after passing through the 3D calibration phantom 10, strikes the 2D detector 23.

For provision of the recorded 2D transmission image, the imaging device 20, in particular the 2D detector 23, has a data interface, which is embodied to form a data connection to the data interface 32 of the device 30 for determining the geometry calibration.

While example embodiments have been described in detail in particular in relation to figures, it should be pointed out that a plurality of variations is possible. It should also be pointed out that the example embodiments merely involve examples that in no way restrict the area of protection, the application and the structure. Instead the preceding description provides the person skilled in the art with a guideline for implementing at least one example embodiment, wherein diverse variations, in particular alternate or additional features and/or variation of the function and/or arrangement of the components described, can be undertaken as required by the person skilled in the art, without deviating in doing so from the subject matter defined in each case in the appended claims in each case, as well as its legal equivalent, and/or without departing from its area of protection.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining assignment data for an imaging device, in which, in a transmission imaging, after passing through a 3D calibration phantom, radiation strikes a 2D detector to create a 2D transmission image of the 3D calibration phantom, the 3D calibration phantom including at least one calibration object with a number of physical calibration elements, spatially arranged such that a descriptor based on the spatial arrangement is projectively invariant during the transmission imaging, the method comprising:
provisioning the 2D transmission image, the at least one calibration object, of the 3D calibration phantom, being shown in the 2D transmission image provisioned;
recognizing the number of physical calibration elements shown in the 2D transmission image to determine calibration elements recognized in the 2D transmission image and a 2D arrangement of the calibration elements;
determining a plurality of subsets of the physical calibration elements recognized, a number of subsets determined corresponding to the number of physical calibration elements of the at least one calibration object;
calculating a respective descriptor, relating to respective calibration elements for each subset of the plurality of subsets determined; and
determining the assignment data, the physical calibration elements recognized for each subset being assigned to the physical calibration elements of the at least one calibration object, for which the respective descriptor computed, and a descriptor relating to the physical calibration elements, differ from one another.

2. The method of claim 1, wherein the 3D calibration phantom includes a plurality of calibration objects, wherein the the plurality of calibration objects include at least one calibration object and a further calibration object, and wherein respective calibration objects of the plurality of calibration objects each include a number of physical calibration elements arranged spatially such that a descriptor based on a spatial arrangement is projectively invariant during the transmission imaging, wherein the descriptor is a strong descriptor; and wherein:
the method is carried out accordingly for the physical calibration elements of the calibration objects of the plurality of calibration objects; and wherein the method further includes:
identifying the calibration objects of the plurality of calibration objects based on the strong descriptor.

3. The method of claim 1, wherein the at least one calibration object includes four physical calibration elements, at least essentially spatially arranged along a first straight line, and wherein:
the descriptor features an arrangement of the four physical calibration elements recognized at least essentially along a 2D straight line and a double ratio for spacings between the four physical calibration elements recognized;
during the determining of the subsets, subsets are determined, for which the four physical calibration elements of a respective subset are arranged at least essentially along a 2D straight line in the 2D transmission image; and
the descriptor for each respective subset of the subsets is furthermore computed by way of the double ratio for the spacings between the four physical calibration elements recognized.

4. The method of claim 1, wherein the at least one calibration object or a further calibration object includes seven physical calibration elements, one physical calibration element, of the seven physical calibration elements, lying on a first straight line and on a second straight line, the first straight line and the second straight line not being parallel, and three further physical calibration elements, of the seven physical calibration elements, each respectively being at least essentially spatially arranged along the first straight line or the second straight line, wherein:
the descriptor features an arrangement of four physical calibration elements recognized at least essentially along a first 2D straight line, and a double ratio for spacings between the four physical calibration elements recognized, and an arrangement of four recognized calibration elements along a second 2D straight line, intersecting with the first 2D straight line in one of the four physical calibration elements, and a second double ratio for spacings between the four recognized calibration elements along a second 2D straight line;
during the determining of the subsets, subsets are determined that have seven physical calibration elements recognized, of which four physical calibration elements are arranged along a first 2D straight line and four physical calibration elements are arranged along a second 2D straight line in the 2D transmission image; and
the descriptor for each respective subset of the subsets is furthermore computed by way of the first double ratio for the spacings of the four physical calibration elements recognized along the first 2D straight line and by way of the double ratio for the spacings of the four physical calibration elements recognized along the second 2D straight line.

5. The method of claim 1, wherein the at least one calibration object includes at least four physical calibration elements further comprising:
defining an order of the at least four physical calibration elements for each subset by way of a criterion for the order;
and wherein the descriptor features the order defined.

6. The method of claim 5, wherein the at least one calibration object or a further calibration object includes at least one different calibration element, the at least one different calibration element compared to other calibration elements differing in relation to a distinction criterion, wherein the method further comprises:
determining the distinction criterion on the 2D transmission image, for each respective calibration element recognized;
determining, for each respective subset of the plurality of subsets, whether calibration elements recognized, of each respective subset, differ relative to the other calibration elements through a respective distinction criterion;
and wherein at least one of
the criterion for the order is based on the distinction criterion and
the descriptor features a position of the at least one different calibration element within the order of the calibration elements.

7. The method of claim 1, wherein the 3D calibration phantom includes a further calibration object with a number of physical calibration elements, accordingly spatially arranged physical and/or embodied corresponding to calibration elements of the at least one calibration object such that the descriptor differs relating to the further calibration object from the descriptor relating to the at least one calibration object, and wherein:
the method for the physical calibration elements of the further calibration object is carried out; and
assigning, provided the number of physical calibration elements is a same number for the at least one calibration object and the further calibration object, the calibration elements of the subset recognized, either to the physical calibration elements of the at least one calibration object or the physical calibration elements of the further calibration object, depending on whether the descriptor computed for the subset differs less from the descriptor of the at least one calibration object, or from the descriptor of the further calibration object.

8. The method of claim 7, further comprising:
calculating a first error value for each respective subset, characterizing a difference between the descriptor computed for the subset and the descriptor of the at least one calibration object or of a further calibration object;
wherein the calibration elements, of one of the subsets recognized, are assigned to the physical calibration elements of the at least one or of the further calibration object depending on whether the first error value respectively calculated is less that a first limit value.

9. The method of claim 1, wherein the method is carried out repeatedly with differently determined subsets of the calibration elements recognized.

10. The method of claim 2, wherein the at least one calibration object includes four physical calibration elements, at least essentially spatially arranged along a first straight line, and wherein:
the descriptor features an arrangement of the four physical calibration elements recognized at least essentially along a 2D straight line and a double ratio for spacings between the four physical calibration elements recognized;
during the determining of the subsets, subsets are determined, for which the four physical calibration elements of a respective subset are arranged at least essentially along a 2D straight line in the 2D transmission image; and
the descriptor for each respective subset of the subsets is furthermore computed by way of the double ratio for the spacings between the four physical calibration elements recognized.

11. The method of claim 2, wherein the at least one calibration object or a further calibration object includes seven physical calibration elements, one physical calibration element, of the seven physical calibration elements, lying on a first straight line and on a second straight line, the first straight line and the second straight line not being parallel, and three further physical calibration elements, of the seven physical calibration elements, each respectively being at least essentially spatially arranged along the first straight line or the second straight line, wherein:
the descriptor features an arrangement of four physical calibration elements recognized at least essentially along a first 2D straight line, and a double ratio for spacings between the four physical calibration elements recognized, and an arrangement of four recognized calibration elements along a second 2D straight line, intersecting with the first 2D straight line in one of the four physical calibration elements, and a second double ratio for spacings between the four recognized calibration elements along a second 2D straight line;
during the determining of the subsets, subsets are determined that have seven physical calibration elements recognized, of which four physical calibration elements are arranged along a first 2D straight line and four physical calibration elements are arranged along a second 2D straight line in the 2D transmission image; and
the descriptor for each respective subset of the subsets is furthermore computed by way of the first double ratio for the spacings of the four physical calibration elements recognized along the first 2D straight line and by way of the double ratio for the spacings of the four physical calibration elements recognized along the second 2D straight line.

12. The method of claim 3, wherein the at least one calibration object or a further calibration object includes seven physical calibration elements, one physical calibration element, of the seven physical calibration elements, lying on a first straight line and on a second straight line, the first straight line and the second straight line not being parallel, and three further physical calibration elements, of the seven physical calibration elements, each respectively being at least essentially spatially arranged along the first straight line or the second straight line, wherein:
the descriptor features an arrangement of four physical calibration elements recognized at least essentially along a first 2D straight line, and a double ratio for spacings between the four physical calibration elements recognized, and an arrangement of four recognized calibration elements along a second 2D straight line, intersecting with the first 2D straight line in one of the four physical calibration elements, and a second double ratio for spacings between the four recognized calibration elements along a second 2D straight line;

during the determining of the subsets, subsets are determined that have seven physical calibration elements recognized, of which four physical calibration elements are arranged along a first 2D straight line and four physical calibration elements are arranged along a second 2D straight line in the 2D transmission image; and the descriptor for each respective subset of the subsets is furthermore computed by way of the first double ratio for the spacings of the four physical calibration elements recognized along the first 2D straight line and by way of the double ratio for the spacings of the four physical calibration elements recognized along the second 2D straight line.

13. The method of claim 2, wherein the at least one calibration object includes at least four physical calibration elements further comprising:

defining an order of the at least four physical calibration elements for each subset by way of a criterion for the order; and wherein the descriptor features the order defined.

14. The method of claim 13, wherein the at least one calibration object or a further calibration object includes at least one different calibration element, the at least one different calibration element compared to other calibration elements differing in relation to a distinction criterion, wherein the method further comprises:

determining the distinction criterion on the 2D transmission image, for each respective calibration element recognized;

determining, for each respective subset of the plurality of subsets, whether calibration elements recognized, of each respective subset, differ relative to the other calibration elements through a respective distinction criterion;

and wherein at least one of the criterion for the order is based on the distinction criterion and the descriptor features a position of the at least one different calibration element within the order of the calibration elements.

15. The method of claim 2, wherein the 3D calibration phantom includes a further calibration object with a number of physical calibration elements, accordingly spatially arranged physical and/or embodied corresponding to calibration elements of the at least one calibration object such that the descriptor differs relating to the further calibration object from the descriptor relating to the at least one calibration object, and wherein:

the method for the physical calibration elements of the further calibration object is carried out; and assigning, provided the number of physical calibration elements is a same number for the at least one calibration object and the further calibration object, the recognized calibration elements of the subset either to the physical calibration elements of the at least one calibration object or the physical calibration elements of the further calibration object, depending on whether the descriptor computed for the subset differs less from the descriptor of the at least one calibration object, or from the descriptor of the further calibration object.

16. A non-transitory computer readable storage medium storing a computer program including program segments which, when executed by a computer, cause the computer to perform the method of claim 1.

* * * * *